(12) United States Patent
Ayliffe et al.

(10) Patent No.: US 11,891,657 B2
(45) Date of Patent: Feb. 6, 2024

(54) ULTRA-SENSITIVE PLATFORM FOR NUCLEIC ACID DETECTION USING A NOVEL METHOD, SCANNING DIGITAL POLYMERASE CHAIN REACTION (PCR)

(71) Applicant: E.I. Spectra, LLC, Ketchum, ID (US)

(72) Inventors: Harold E. Ayliffe, Ketchum, ID (US); Donald O'Neil, Ketchum, ID (US)

(73) Assignee: Orflo Technologies LLC, Ketchum, ID (US)

( * ) Notice: Subject to any disclaimer, the term of this patent is extended or adjusted under 35 U.S.C. 154(b) by 583 days.

(21) Appl. No.: 17/093,429

(22) Filed: Nov. 9, 2020

(65) Prior Publication Data

US 2021/0054441 A1    Feb. 25, 2021

Related U.S. Application Data

(63) Continuation of application No. 16/184,863, filed on Nov. 8, 2018, now abandoned.

(60) Provisional application No. 62/584,055, filed on Nov. 9, 2017.

(51) Int. Cl.
*C12Q 1/686* (2018.01)
*C12Q 1/6848* (2018.01)
*C12Q 1/6827* (2018.01)

(52) U.S. Cl.
CPC ........... *C12Q 1/686* (2013.01); *C12Q 1/6827* (2013.01); *C12Q 1/6848* (2013.01)

(58) Field of Classification Search
CPC .... C12Q 1/686; C12Q 1/6827; C12Q 1/6848; C12Q 2527/146; C12Q 2563/159
See application file for complete search history.

(56) References Cited

U.S. PATENT DOCUMENTS

| | | | | |
|---|---|---|---|---|
| 6,899,137 B2 * | 5/2005 | Unger | ................. | B81C 1/00119 137/833 |
| 2013/0327957 A1 * | 12/2013 | Ayliffe | ................... | G01N 15/12 250/200 |

OTHER PUBLICATIONS

Hoffman et al., Solid-phase PCR in a picowell array for immobilizing and arraying 100 000 PCR products to a microscope slide, 2012, Lab Chip, 2012, 12, 3049-3054 (Year: 2012).*

* cited by examiner

*Primary Examiner* — Narayan K Bhat
(74) *Attorney, Agent, or Firm* — FisherBroyles, LLP

(57) ABSTRACT

A method for analyzing a target nucleic acid includes diluting nucleic acid targets and filling pico to femto-liter sized wells such that they contain a single target nucleic acid and one or more amplification reagents, amplifying the target in the individual wells, distinguishing wells containing amplicon from the target and amplicon from a variant of the target generated by polymerase error by using two differently labeled-hybridization probes, one hybridizing to the target and one hybridizing to a specific variant of the target; and analyzing target amplicons.

6 Claims, 11 Drawing Sheets

3-STEP Work Flow

1 - Prepare PCR Supermix and Dispense onto MicroWell Chip.

2 - Seal Individual MicroWells.

3 - Insert Slides into sdPCR System and START.

*System Automatically:*
- *Aligns*
- *Performs PCR*
- *Scans Sample*
- *Reports Results.*

FIG. 5

3. Insert into sdPCR System
System Starts Automatically

Run up to 9 Chips

Integrated sdPCR System sdPCR Rendering

Specifications:

- Runs up to 9 MicroWell Chips
- Performs PCR
- Aligns Laser to each Chip
- Two Color Fluorescence
- Results compiled and Summary is displayed on Unit
- Battery Powered
- USB-on-the-GO
- Utilizes Moxi GO Light Engine

ULTRA-SENSITIVE PLATFORM FOR NUCLEIC ACID DETECTION USING A NOVEL METHOD, SCANNING DIGITAL POLYMERASE CHAIN REACTION (PCR)

PRIORITY CLAIM

This application is a continuation of U.S. application Ser. No. 16/184,863 filed Nov. 8, 2018; which claims priority from U.S. Prov. Pat. Appl. No. 62/584,055 filed Nov. 9, 2017. The above-referenced applications are hereby incorporated by reference in their entireties as if fully set forth herein.

BRIEF DESCRIPTION OF THE DRAWING FIGURES

Preferred and alternative embodiments of the present invention are described in detail below with reference to the following drawing figures.

FIGS. 5-11 illustrate a workflow and associated system according to an embodiment of the invention.

DETAILED DESCRIPTION

Figure 1:
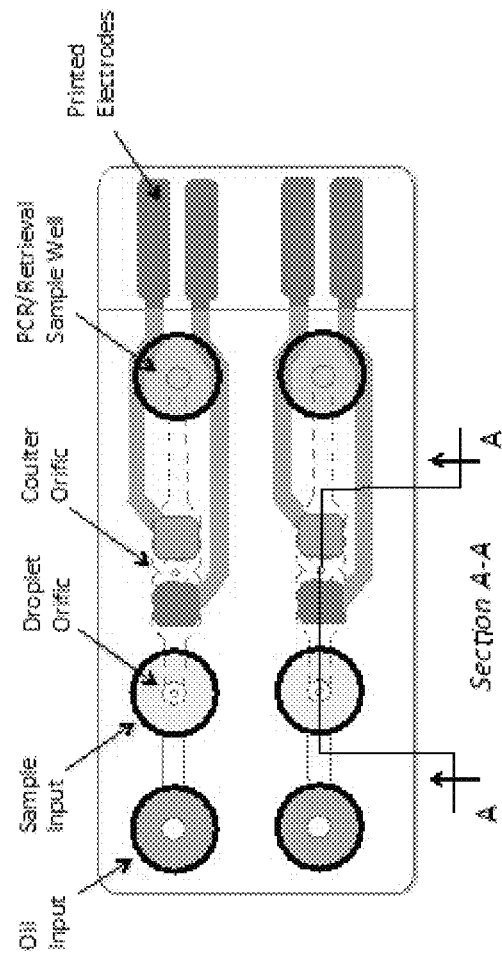
FIG. 1 illustrates a top view of a multi-layer, thin-film cassette according to an embodiment of the invention.

There is a clear need in biological related sciences to determine the presence of low abundance nucleic acid sequences for gene expression analysis, mRNA analysis, vial load determination, and pathogen detection, among others. There is also a strong need in research for absolute quantification of target nucleic acid sequences. Absolute quantification is possible by partitioning a quantitative PCR reaction into 10s of thousands of individual femtoliter volumes, or wells. Each well contains a single target molecule (positive) or no target molecule (negative). Sample partitioning allows sensitive, specific detection of single template molecules. The partitioning mitigates the effects of target competition, making digital PCR amplification less susceptible to inhibition and greatly improving the discriminatory capacity of assays.

The only other currently available technology to perform absolute quantification of nucleic acid sequences (also known as Digital PCR) is to split the PCR reaction materials into thousands of individual emulsion droplets. This process is expensive, complicated, and cumbersome to perform and requires three separate instruments, a droplet generator, a thermocycler (for PC), and a flow-based droplet analyzer.

Embodiments include a novel structure and method for performing digital PCR using a low-cost, easy-to-use consumable and a combined thermocycler/analyzer. A PCR supermix is deposited into a slide containing approximately 20,000 microwells with volumes on the order of femtoliters. Capping layers, such as plastic or glass, are then added to seal each well to form individual reaction chambers for subsequent PCR.

Once prepared, the femtoliter well chips may be placed into a fully integrated system (it can also be done using two separate systems, one for PCR and one for the analysis) that performs the thermalcycling required for PCR and then the analysis. The system may comprise a laser with a beam focused to interrogate only one well at a time, at least one photodetector for measuring the emitted fluorescence from each individual well, a laser steering assembly for scanning the laser over the 20,000+ wells, and a programmable microcontroller. The system will also likely need to be able to "align" the laser to the consumable so that it "knows" where all of the wells are located. To do this, the preferred embodiment will be a photodiode placed on the opposite side (likely under) the femtoliter well consumable.

Additionally, there is a clear need in biological related sciences to determine the presence of low abundance nucleic acid sequences for gene expression analysis, mRNA analysis, vial load determination, and pathogen detection, among others. There is also a strong need in research for absolute quantification of target nucleic acid sequences. Absolute quantification is possible by partitioning a quantitative PCR into 10s of thousands of individual picoliter volumes, or wells. Each well contains a single target molecule (positive) or no target molecule (negative). Sample partitioning allows sensitive, specific detection of single template molecules (i.e., the molecule of interest). The partitioning mitigates the effects of target competition, making digital PCR amplification less susceptible to inhibition and greatly improving the discriminatory capacity of assays.

The only other currently available technology to perform absolute quantification of nucleic acid sequences (also known as Digital PCR) is to split the PCR reaction materials into thousands of individual emulsion droplets. This process is expensive, complicated, and cumbersome to perform and requires three separate instruments, a droplet generator, a thermocycler (for PC), and a flow-based droplet analyzer.

Embodiments include a structure and method for performing digital PCR using a low-cost, easy-to-use consumable and a combined thermocycler/analyzer. This is done by creating emulsion droplets using a low-cost, thin-film technology with an optional method to measure the size of the droplets, and to some extent, the contents of the droplets, just downstream of their production, all within the same structure/cassette. By combining precision laser processing and multi-layer laminates, an embodiment provides low-cost, high-efficiency emulsion droplet generating cassettes (see FIG. 1 and FIG. 2). This 3-D, thin-film structure is unique and allows for the sample well to be positioned directly over the droplet generating orifice. By locating the sample well directly over the droplet orifice, the suspended cells can be allowed to settle to the bottom, via gravity, to greatly increase the resulting cell-in-droplet efficiency.

Preferably, within the same cassette, it is also possible to incorporate a current Coulter-style particle interrogation structure (which may be described in one or more of U.S. Pat. Nos. 7,417,418, 7,515,268, 7,520,164, 7,579,823, 8,171,778, 8,329,437, and 8,804,105). When the optional Coulter orifice is added just downstream of the droplet fabricator, it is possible to measure the size of the particle using direct current (DC) and the contents of the droplet using simultaneous alternating current (AC). It is also feasible to use just DC or just AC current instead of both simultaneously.

An embodiment includes a system that works with the above described emulsion droplet generating cassette that will drive the droplet fabrication with Coulter orifice feedback to help control droplet size and (in some cases) single-cell encapsulation efficiency and/or determination. Control of droplet size, frequency, and efficiency can be accomplished by varying the applied pneumatic pressure and/or vacuum to the cassette. This system has the optional ability to perform the necessary thermal cycling to PRC on the prepared droplets when desired. This is done by thermally cycling the Retrieval Sample Well (FIG. 1) prior to removal of the cassette from the system.

Alternate embodiments may include:

Instead of using the Coulter orifice for downstream QC and feedback, it is possible to run the sample through a flow cytometer immediately after fabrication to determine approximate droplet size and contents. This may be done with side-scatter (or forward light collection) and fluorescence.

The cassette could be simplified to have just the droplet orifice structure with no feedback.

FIG. 1 illustrates the multi-layer, thin-film cassette having the high-efficiency droplet fabrication orifice, the downstream Coulter orifice (for size and content determination), and the Retrieval Sample Well where optional PCR can be performed.

Figure 2:
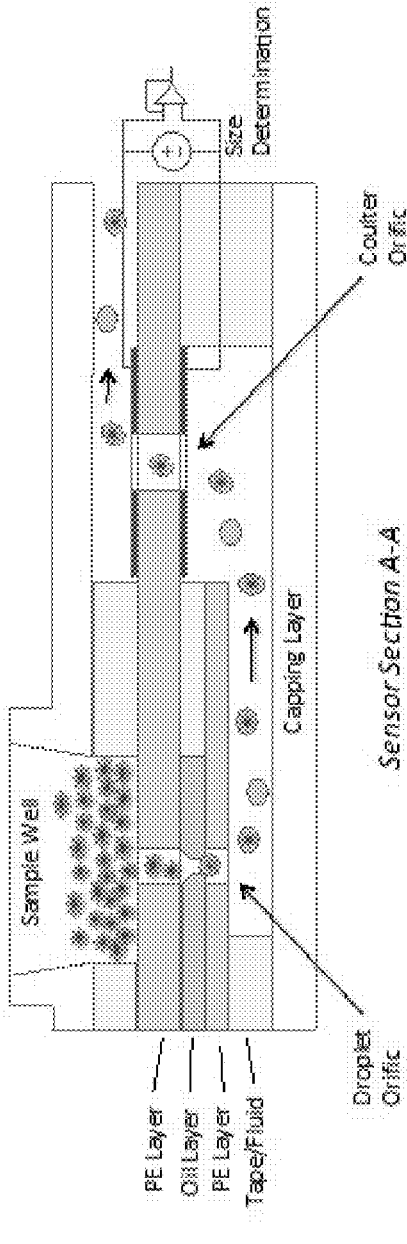
FIG. 2 illustrates a cross-section of the high-efficiency single-cell droplet generating cassette of FIG. 1.

FIG. 2 illustrates a cross-section of the high-efficiency single-cell droplet generating cassette (from FIG. 1) showing the layers optionally advantageous to perform the emulsion droplet production and the downstream Coulter orifice for electric impedance-based particle analysis.

One of the major challenges in forming droplets containing single cells, is the inability to control when a droplet should be formed such that it contains a desired cell. State of the art technologies use statistical models and cell concentrations to drive the efficiency of cell/droplets. Currently available commercial systems claim efficiencies of up to only 60%, and actual efficiencies can be much lower. Because the success of downstream single-cell sequencing operations depends on the success, efficiency, and purity, of correctly produced single-cell droplets, there is a strong market need for a highly efficient single-cell droplet generator that can produce droplets with desired cells (only) on demand. In addition, there are currently no commercially available droplet systems with built-in quality control checks of any kind.

An embodiment includes the multilayer thin-film droplet generator with the addition of an epi fluorescence system to detect the presence of the cells of interest as they approach the droplet generating orifice. Also added is an electrical actuator (such as a piezoelectric actuator) capable of creating a transient pressure pulse to selectively force the desired cells through the droplet generating orifice, thereby only creating droplets containing cells, and driving efficiency towards 100%.

Figure 3:
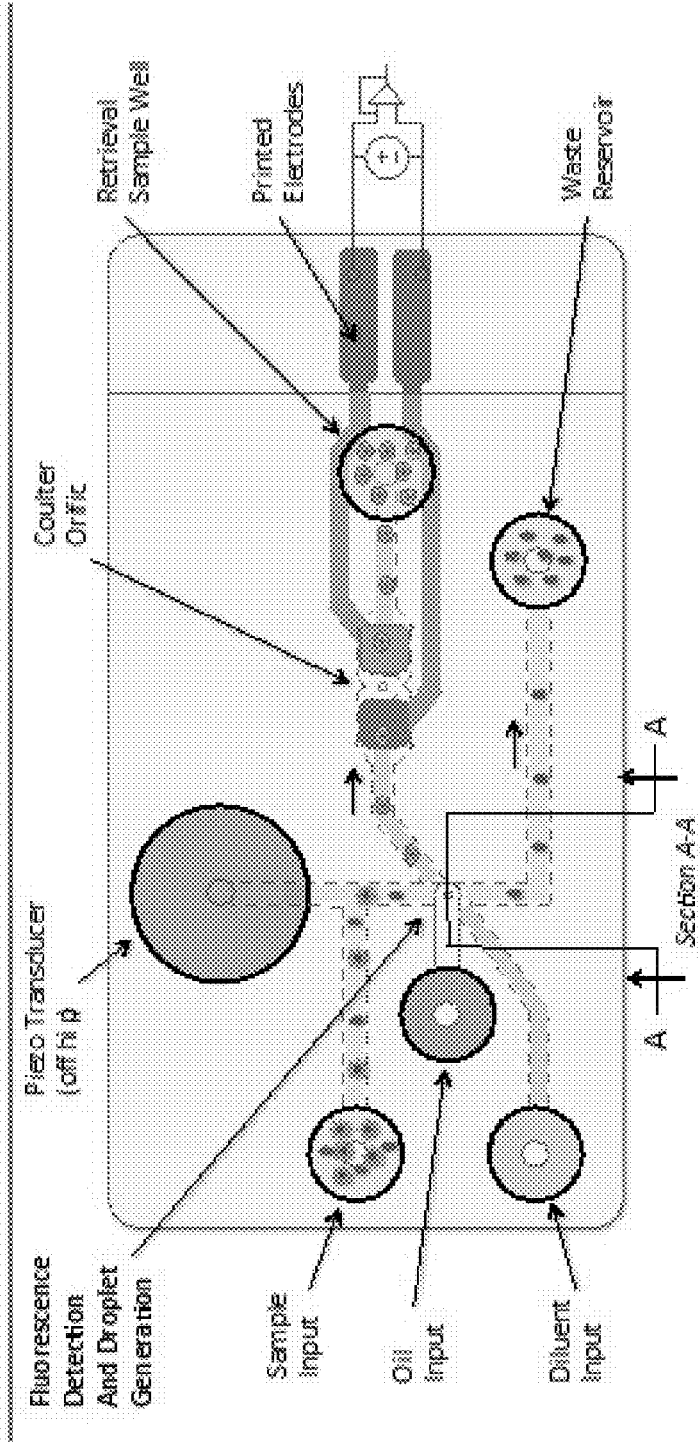
FIG. 3 illustrates a top view schematic of an active single-cell droplet generator according to an embodiment of the invention.
Figure 4:
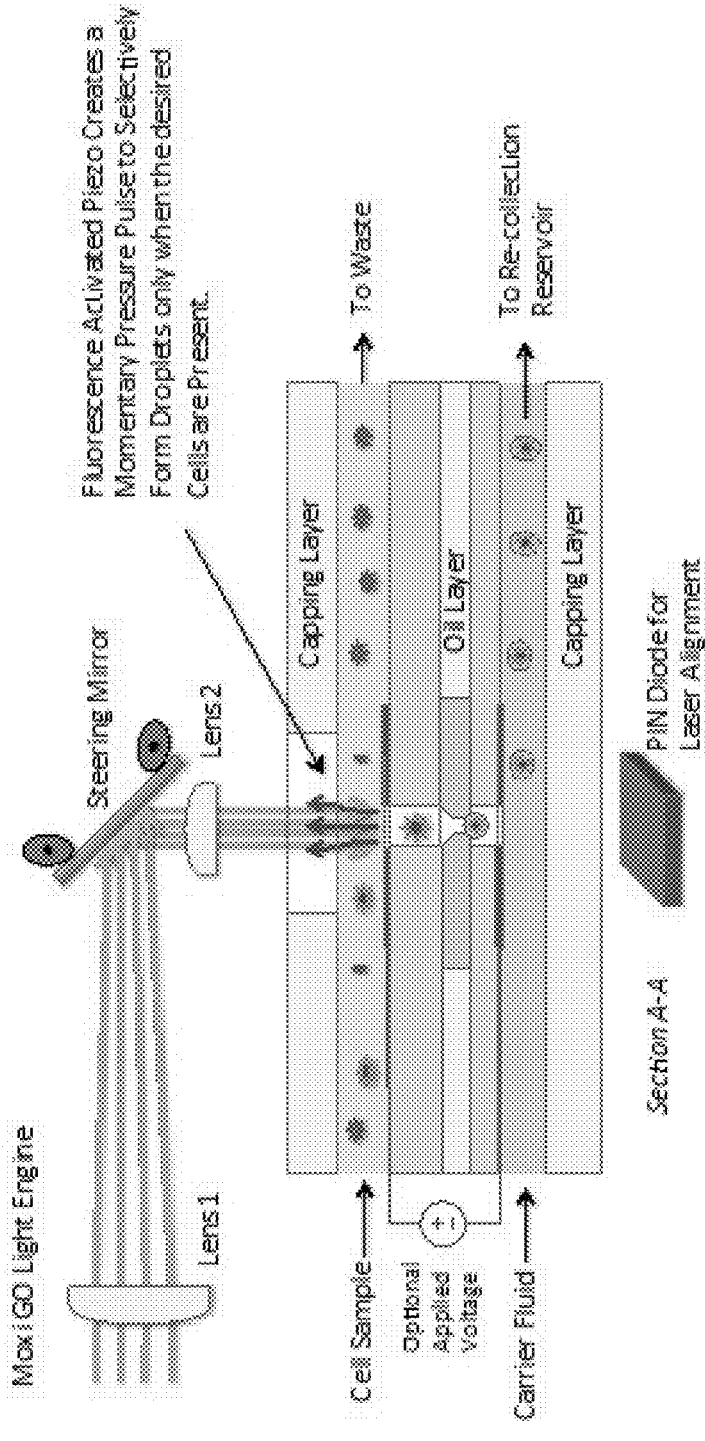
FIG. 4 illustrates a cross-section view of the active single-cell droplet generator of FIG. 3.
Figure 6:
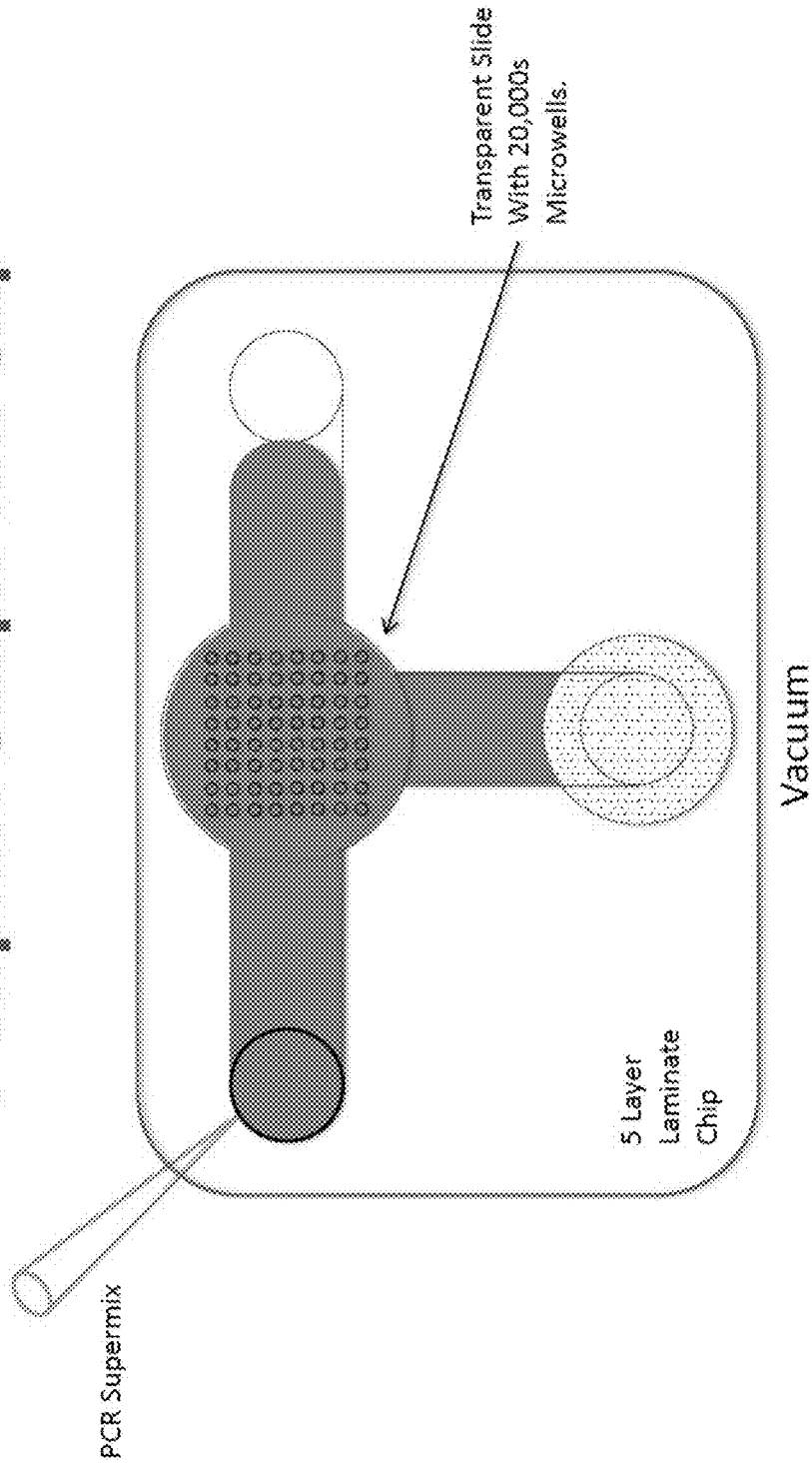
Figure 7:
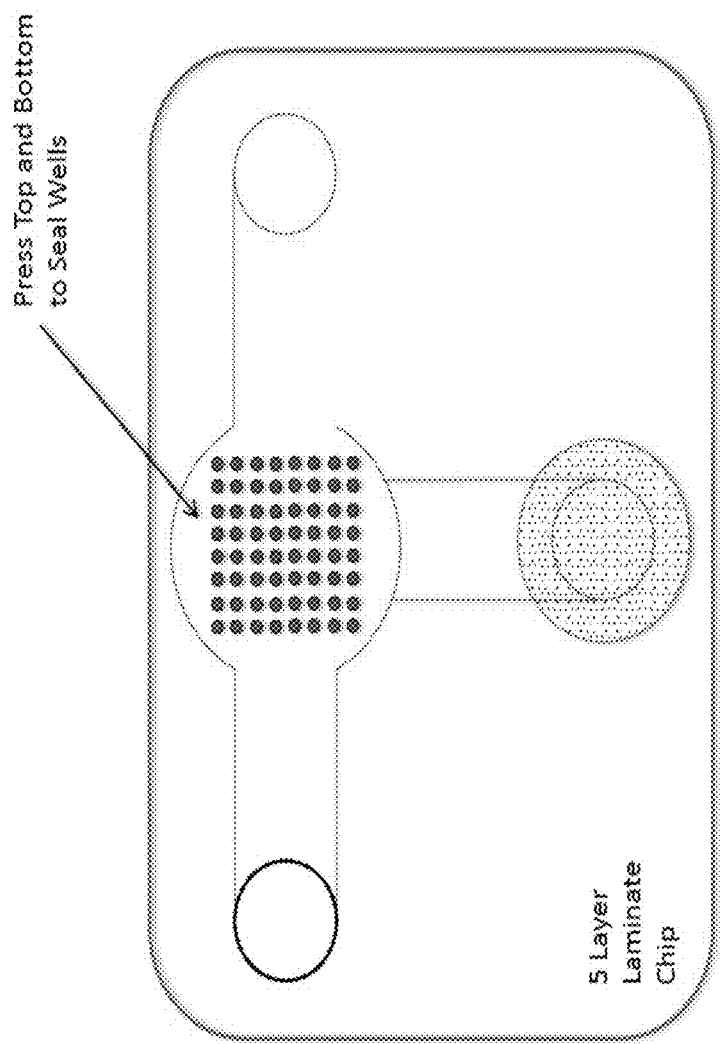
Figure 8:
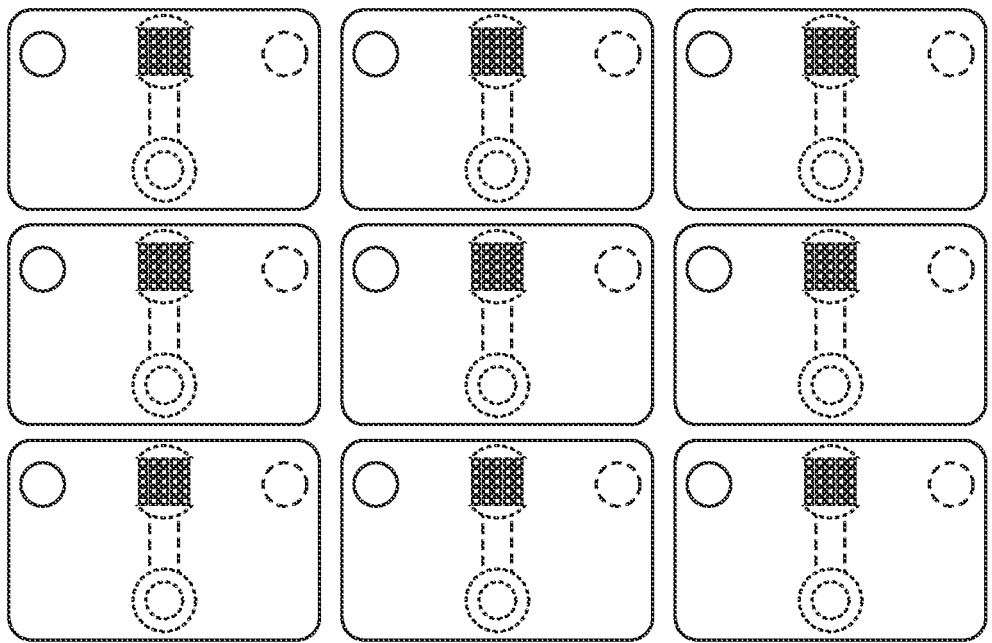
Figure 8:
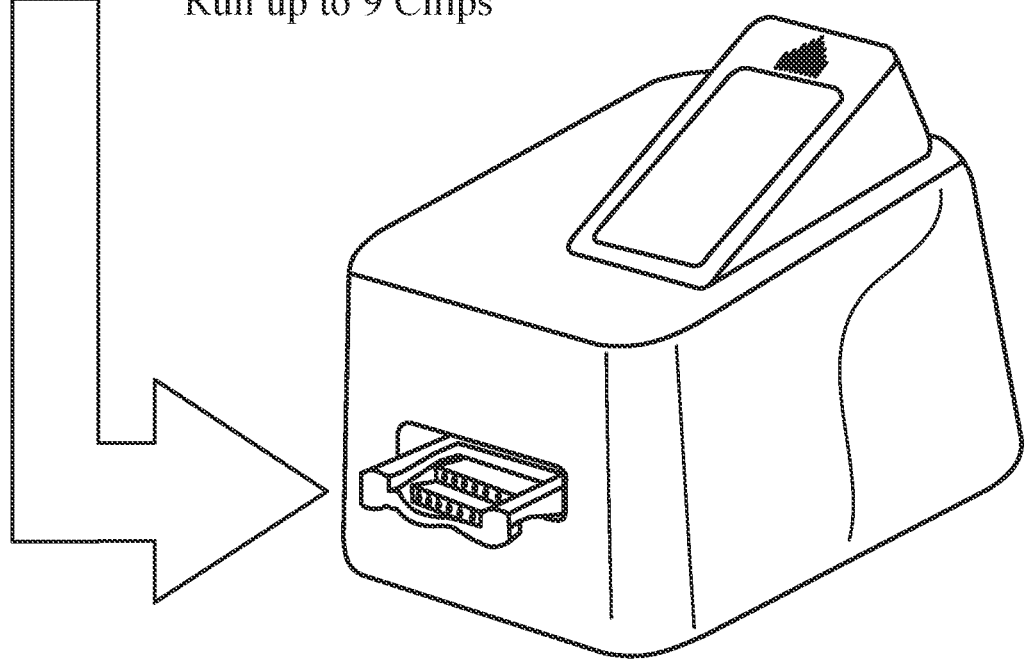
Figure 9:
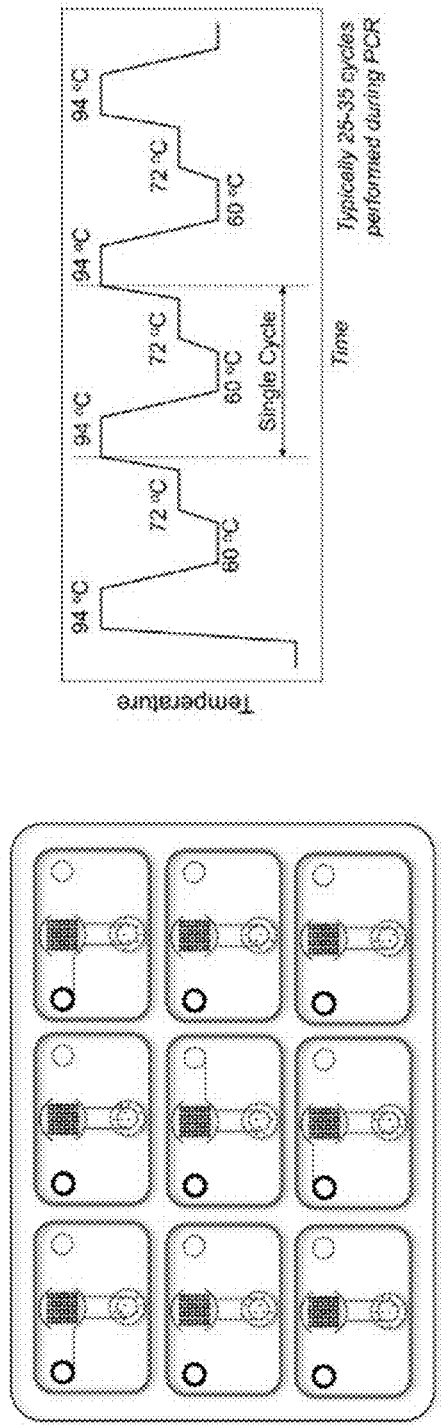
Figure 10:
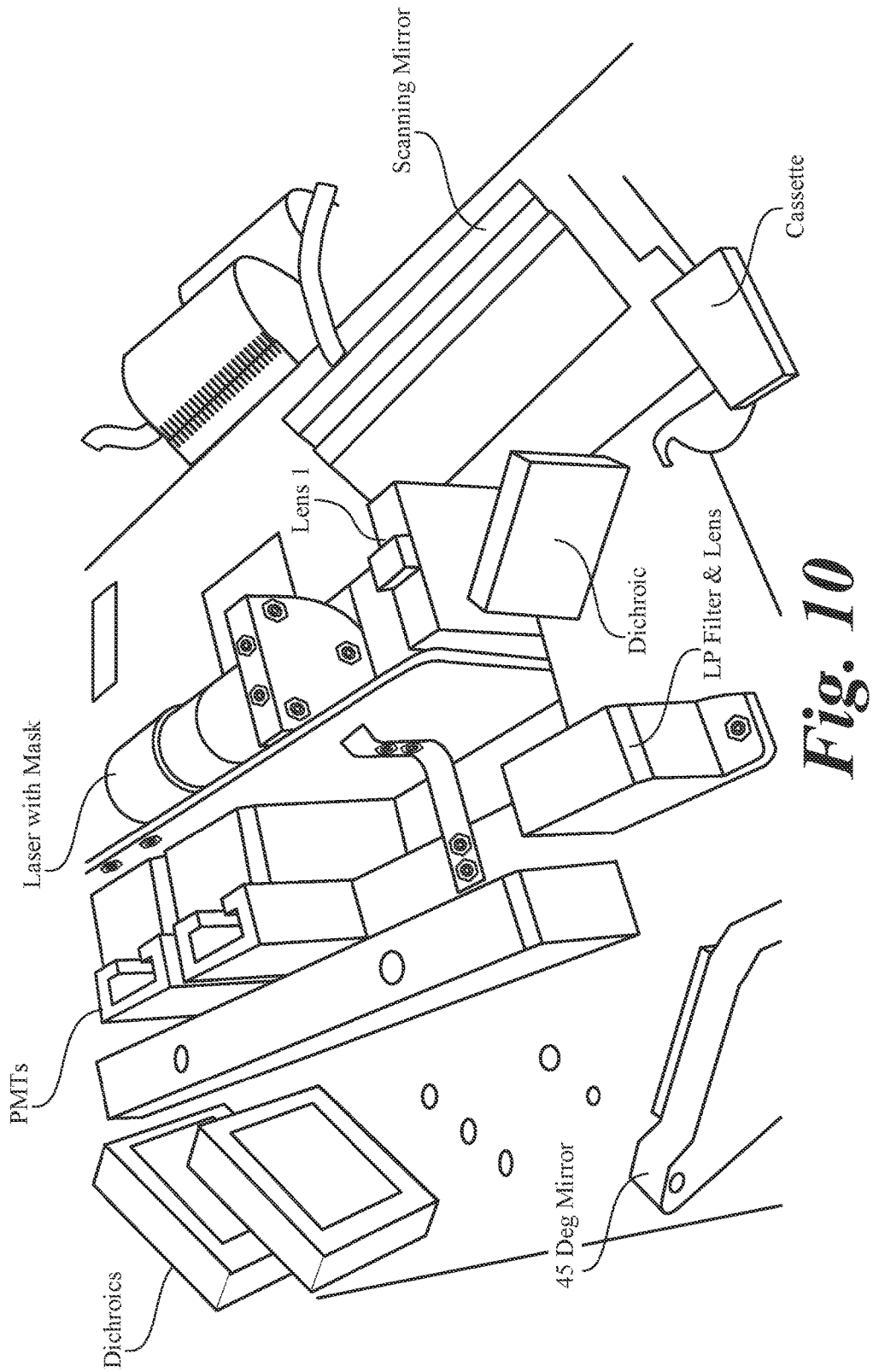
Figure 11:
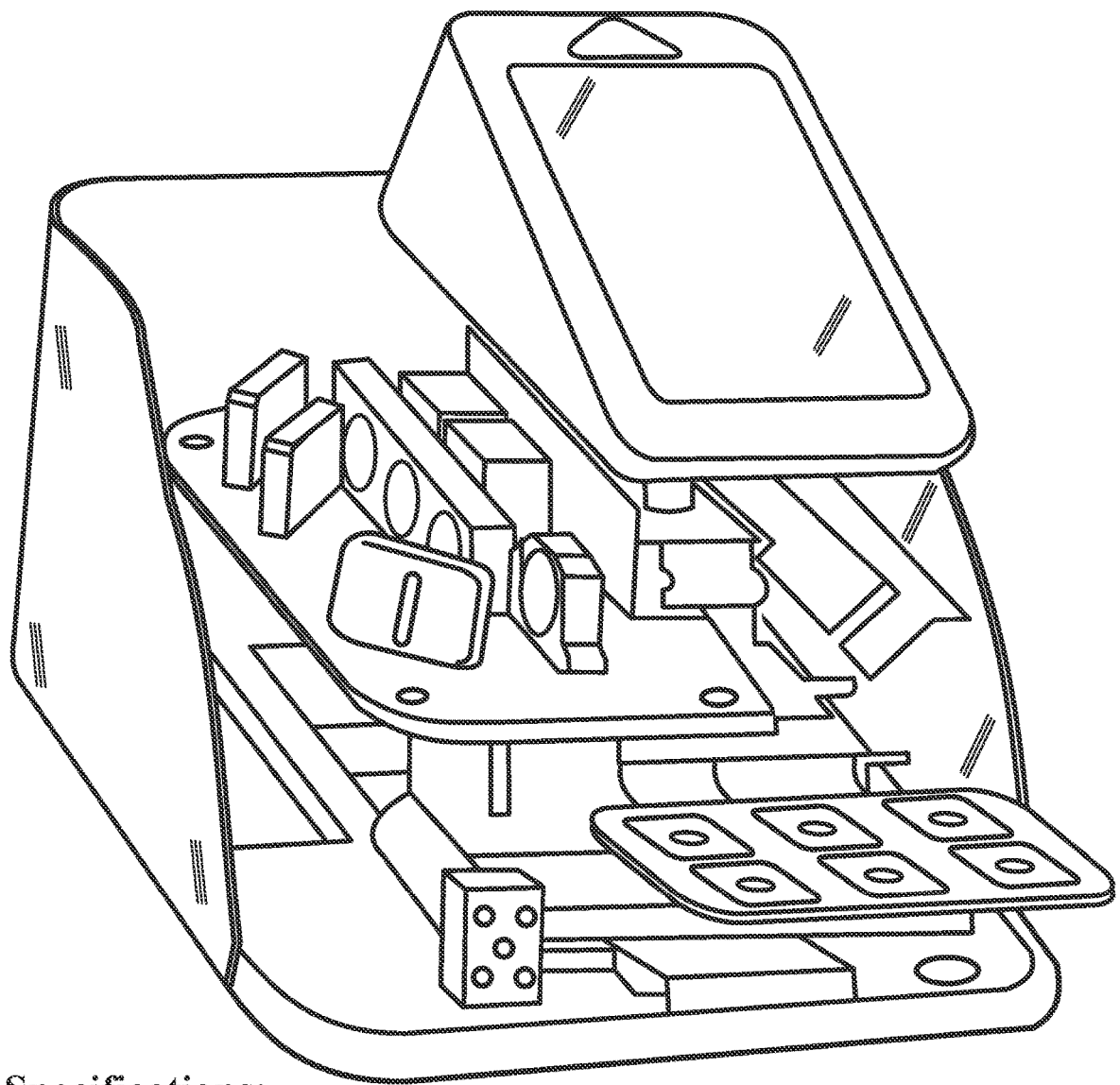

Cell/droplet efficiency, as well as purity (i.e., only desired cells and not debris) is absolutely critical as the success of downstream DNA sequencing operations relies heavily on both the percent efficiency and droplet purity. The best commercially available single-cell droplet systems have efficiencies approaching only 60%, and actual efficiencies are typically much lower. FIG. 3 shows the top-view of one possible configuration for an active single cell droplet generator. FIG. 4 is a cross-section view of the droplet generator orifice showing the seven thin film layers. In the preferred embodiment, the fabricated droplets flow through a downstream Coulter orifice to measure their size (DC current) and contents (i.e., if a cell is inside) using AC current. The Coulter data can be used in real-time to adjust the input variables (pressure transducer timing, input pressures and/or vacuums, and optional DC voltage across the droplet orifice), thereby manipulating the size of the droplets and the resulting single-cell efficiency. Such a system will become a powerful tool in the rapidly growing field of single-cell genomics.

FIG. 3 illustrates a top view schematic of an active single-cell droplet generator. Epi fluorescence illumination is directed to the droplet generator orifice. When a cell of interest approaches the droplet generator orifice, the piezoelectric transducer is activated and the transient pressure differential forces the cell downward, through the droplet generator, thereby only producing droplets with the desired cells.

FIG. 4 illustrates a cross-section view of the active single-cell droplet generator from FIG. 3 in a seven-layer thin-film cassette. The cassette is fabricated with two outer translucent capping layers, three double-sided pressure sensitive adhesive layers with fluidic channel, and a central polyester layer. Cells in suspension flow across and over the droplet orifice and into a waste reservoir. When a cell of interest approaches the droplet generator orifice, the piezoelectric transducer is activated and the transient pressure differential forces the cell downward, through the droplet generator, thereby only producing droplets with the desired cells. The resulting single-cell droplets flow into a downstream though an optional Coulter orifice where the size can be measured using direct current and the droplet constituents (i.e., if a cell is present or not) can be determined using high-frequency alternating current. Once the droplets pass the Coulter orifice they flow to a reservoir where they are re-collected and used for subsequent DNA sequencing.

While the preferred embodiment of the invention has been illustrated and described, as noted above, many changes can be made without departing from the spirit and scope of the invention. Accordingly, the invention is not limited except as by the appended claims.

What is claimed is:

1. A system for detecting a target nucleic acid, comprising:
   a cassette, the cassette comprising a sample input configured to receive an emulsion containing at least one target molecule and at least one non-target molecule, the cassette further comprising at least one intermediate layer, the cassette further comprising at least one capping layer, the at least one capping layer and intermediate layer defining at least one chamber, the at least one intermediate layer having a droplet orifice formed therethrough allowing fluid communication between the sample input and a first chamber of the at least one chamber, the at least one intermediate layer defining at least one egress orifice allowing the emulsion to exit the at least one chamber; and
   a flow cytometer having an interior configured to receive at least a portion of the cassette, the flow cytometer configured to identify the at least one target molecule.

2. The system of claim 1, wherein the droplet orifice is sized to pass the emulsion molecules from the sample input to the chamber in single file.

3. The system of claim 1, wherein the flow cytometer identifies the at least one target molecule by scanning molecules of the emulsion with a laser.

4. The system of claim 1, wherein the egress orifice is part of a Coulter-style particle interrogation structure that interrogates each molecule of the emulsion passing through the egress orifice.

5. The system of claim 1, further comprising a pressure generator configured to create emulsion droplets by drawing the emulsion molecules from the sample input through the egress orifice.

6. The system of claim 1, wherein the cassette further comprises a piezoelectric transducer configured to cause only the identified at least one target molecule to be drawn through the droplet orifice.

* * * * *